United States Patent [19]

Lee et al.

[11] Patent Number: 5,319,123

[45] Date of Patent: Jun. 7, 1994

[54] PROCESS FOR PREPARING SUBSTITUTED N-OXY-IMIDIC ACID DERIVATIVES

[75] Inventors: George T. Lee, Bloomfield; Ustun B. Sunay, Netcong; Prasad K. Kapa, Parsippany, all of N.J.

[73] Assignee: Sandoz Ltd., Basel, Switzerland

[21] Appl. No.: 701,933

[22] Filed: May 17, 1991

Related U.S. Application Data

[63] Continuation-in-part of Ser. No. 537,408, Jun. 13, 1990, abandoned.

[51] Int. Cl.$^5$ .............................................. C07C 249/00
[52] U.S. Cl. .......................................... 558/7; 560/51
[58] Field of Search .............................. 558/7; 560/51

[56] References Cited

FOREIGN PATENT DOCUMENTS 273432 6/1988 European Pat. Off. .
1226864 11/1989 Japan .

*Primary Examiner*—Paul J. Killos
*Attorney, Agent, or Firm*—Robert S. Honor; Melvyn M. Kassenoff; Thomas O. McGovern

[57] ABSTRACT

N-oxy substituted imidic acid derivative of the formula

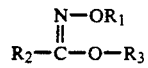

where $R_1$, $R_2$ and $R_3$ are alkyl and aryl substituents, which are useful as antidiabetic and hypolipidemic agents are prepared by the following procedure:

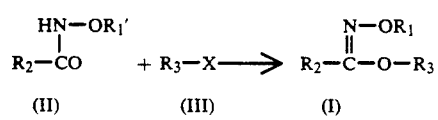

where X is chlorine, bromine, or iodine, and $R_1'$ is the same as $R_1$ but with any hydroxy or carboxy groups present protected by a hydroxy or carboxy protecting group and, when $R_1'$ is a protected hydroxy or carboxy substituent, deprotecting the substituent.

13 Claims, No Drawings

PROCESS FOR PREPARING SUBSTITUTED N-OXY-IMIDIC ACID DERIVATIVES

This is a continuation-in-part of U.S. patent application Ser. No. 537,408, filed Jun. 13, 1990, now abandoned.

This invention relates to processes for preparing N-oxy substituted imidic acid derivatives, which are useful as pharmaceutical agents. More particularly, this invention concerns processes for preparing N-alkoxy and aryloxy imino acid anhydrides, which are useful as anti-diabetic and hypolipidemic agents.

The compounds of this invention may be represented by the following structural formula:

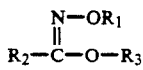  (I)

where
$R_1$ is alkyl of 1 to 6 carbon atoms, for example, methyl, ethyl, and isopropyl; alkenyl of 3 to 5 carbon atoms whereon the double bond is separated from the oxygen atom by at least 2 carbon atoms, for example, allyl; alkyl of 2 to 8 carbon atoms mono- or polysubstituted by up to 7 hydroxy groups on other than the α-carbon, for example, hydroxyethyl and 2,3-dihydroxypropyl; alkyl of 2 to 8 carbon atoms mono- or poly substituted by up to 7 lower alkoxy groups, that is, alkoxy of 1 to 4 carbon atoms on other than the α-carbon, for example, methoxyethyl; carboxyalkyl of 2 to 6 carbon atoms, for example, carboxymethyl, carboxyethyl, carboxypropyl and 1,1-dimethylcarboxyethyl; 4-pivaloylbenzyl; or

where
$R_4$ and $R_5$ are each independently hydrogen, halogen, hydroxy, lower alkyl as defined above, or lower alkoxy as defined above and
n is 0 or an integer from 1 to 5,
$R_2$ is lower alkyl as defined above or a substituent of the formula

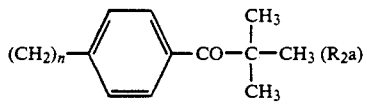

where
n, $R_4$, and $R_5$ are as defined above, and $R_3$ is $R_2$ or CO-$R_2$,
where
$R_2$ is as defined above,
with the provisos:
a) when $R_3$ is $R_{1a}$ or $R_{2a}$, n is an integer of 1 to 5 therein;
b) when $R_3$ is CO-$R_{1a}$ or CO-$R_{2a}$, n is 0 therein; and
c) when $R_3$ is other than CO-$R_{2a}$, $R_2$ is $R_{2a}$ in which n is 0 therein, or when $R_1$ is carboxyalkyl of 2 to 6 carbon atoms, a pharmaceutically acceptable and physiologically hydrolysable ester or a pharmaceutically acceptable salt thereof.

In accordance with the provisos for the compounds of formula (I), either $R_2$ is as defined above and $R_3$ is 4-pivaloylbenzoyl or $R_2$ is 4-pivaloylphenyl and $R_3$ is lower alkyl, alkanoyl of 2 to 5 carbon atoms, aralkyl of formula $R_{1a}$ or $R_{2a}$ in which n is 1 to 5, or aroyl of formula CO-$R_{1a}$ in which n is 0. It will be understood that when $R_1$ is alkyl of 2 to 8 carbon atoms, substituted by up to 7 hydroxy or alkoxy groups, each substituted carbon contain only one hydroxy or alkoxy group.

Only one isomeric form is shown in the structure of the compounds of formula (I) above. However, the compounds can exist in the form of E or Z geometrical isomers, which can be prepared as such or readily separated and recovered by conventional techniques from isomeric mixtures. All such isomeric forms are included in the scope of this invention. The compounds obtained in the present invention are predominantly in the form of a single isomer.

Substituent $R_1$ is preferably methyl; alkyl of 2 to 6 carbon atoms substituted with 1 to 4 hydroxy groups, especially hydroxyethyl and 2,3-dihydroxypropyl; or alkyl of 2 to 6 carbon atoms substituted with 1 to 4 lower alkoxy groups, especially, methoxyethyl. Substituents $R_2$ and $R_3$ are preferably 4-pivaloylphenyl and 4-pivaloylbenzoyl respectively. Halogen can be flourine, chlorine, bromine, or iodine, especially flourine or chlorine, in particular, chlorine.

The compound of formula (I) may be prepared in accordance with the following reaction scheme:

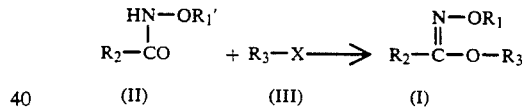

where
X is a leaving group, for example, chlorine, bromine, or iodine,
$R_1'$ is the same as $R_1$ but with the hydroxy or carboxy groups of any hydroxy alkyl, hydroxy aryl or carboxy alkyl substituent protected by a hydroxy protecting group, and
$R_2$ and $R_3$ are as defined above.

The compounds of formula (I) are prepared by reacting a compound of formula (II) with a compound of formula (III) in the presence of a base; and when $R_1$, is a protected hydroxy alkyl, hydroxy aryl, or carboxyalkyl substituent, deprotecting the substituent. The protecting group for the hydroxy alkyl and hydroxy aryl substituents can be any hydroxy protecting group, such as for example, p-anisyldiphenylmethyl for mono hydroxy alkyl or aryl substituents and acetonide forming agents, such as 2,2-dimethoxy propane for 1,2- or 1,3-diols. Protecting groups for the carboxyalkyl substituents are preferably the lower alkyl esters, in particular the tertiary butyl ester. It will be appreciated that where the compound of formula (I) is desired in the form of a pharmaceutically acceptable ester, the protected carboxyalkyl can be in the desired ester form. The protecting groups can be removed by standard deprotecting techniques, such as acid hydrolysis, as described below or in the examples. The base may be an inorganic base, for example, an alkali metal hydride such as potassium hydride, or an alkali metal hydroxide or carbonate such as sodium hydroxide or potassium carbonate, preferably in a ratio of from 1:1 to 2:1 on a molar basis. In the process of the present invention the reaction is carried out in the presence of a hindered organic base such as a tertiary amine, in particular, triethylamine. The ratio of hindered base to compound (II) is 1 to 5 moles of base per mole of compound (II), preferably, 1 to 2 moles of base per mole of compound (II). The solvent used is preferably a non-polar solvent, for example aliphatic and aromatic hydrocarbons, such as hexane, benzene, toluene, etc., especially toluene; halogenated hydrocarbons, such as methylene chloride, ethers, such as dioxane; and tetrahydrofuran. It is also preferred that reaction be run at temperatures between about $-40°$ C. to about $90°$ C., especially about $-20°$ C. to about $60°$, in particular $-10°$ C. to $30°$ C. The time of the reaction is not critical, but it is preferred that the reaction be run for about 1 to 16 hours, especially 1 to 4 hours, in particular 1 to 2 hours. The compound of formula (I) is isolated by conventional techniques, for example, evaporation and/or column chromatography.

The preferred process for preparing the compounds of formula (I) in which $R_2$ is 4-pivaloylphenyl and $R_3$ is 4-pivaloylbenzoyl, is a one-pot process in accordance with the following reaction scheme:

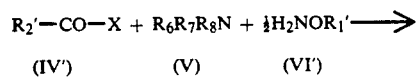

(IV')   (V)   (VI')

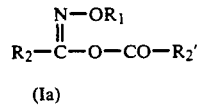

(Ia)

where
$R_6$, $R_7$, and $R_8$ are each independently lower alkyl or aryl, for example, benzyl, and
X, and $R_1'$, are as defined above and $R_2'$ is 4-pivaloylphenyl, The compounds of formula (Ia) are prepared by reacting a compound of formula (IV') in a non-polar solvent with an aqueous solution of the tertiary amine of formula (V) and ½ mole of the compound of formula (VI) per mole of the compound of formula (IV'); and when $R_1'$ is a protected hydroxy alkyl, hydroxy aryl, or carboxy alkyl substituent, deprotecting the substituent. It is preferred that the reaction be carried out in excess tertiary amine of formula (V), in particular, about 2 to 3 moles of the compound of formula (V) per mole of the acid chloride of formula (IV'). Hydroxy and carboxy protecting groups and non-polar solvents, which can be used, are the same as in the above process for preparing the compounds of formula (I). The non-polar solvent is preferably toluene. In the process, it is also preferred that the reaction be carried out with stirring at temperatures between about $-10°$ C. to about $40°$ C., starting at $-10°$ to $-5°$ C. while adding the reactants over a period of about 40 to 60 minutes, and then allowing the temperature to rise slowly to about $30°$ to $40°$ C. over a period of 1 to 2 hours. The final product is isolated by conventional techniques for example evaporation and recrystallization, preferably, from 5% toluene in methanol.

The compound formula (II) can be prepared in accordance with the following reaction scheme:

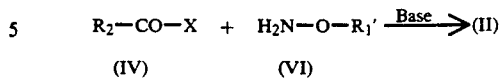

when $R_1'$, $R_2$ and X are as defined above.

The compounds of formula (II) are prepared by reacting a compound of formula (IV) with a compound of formula (VI) in the presence of a base. The base can be an organic or inorganic base such as those used in preparing the compound of formula (I) above. Although a solvent is not required, it is preferred that the reaction be carried out by reacting a solution of a compound of formula (IV) in an inert solvent, for example, aliphatic and aromatic hydrocarbons, such as hexane, benzene, toluene, etc.; halogenated hydrocarbons, such as methylene chloride; ethers such as dioxane; and tetrahydrofuran with an aqueous solution of the compound of formula (VI). The aqueous solution of the compound of formula (VI) may contain a water miscible cosolvent such as tetrahydrofuran. It is preferred that the reaction be run at temperatures between about $-50°$ C. to about $50°$ C., especially about $-15°$ C. to about $20°$ C. The time of the reaction is not critical, but it is preferred that the reaction be run while stirring for about 15 minutes to 4 hours, especially 30 minutes to 1 hour. The compound of formula (II) is isolated by conventional techniques, for example, evaporation and recrystallization.

The compounds of formula II may also be prepared in accordance with the following reaction scheme:

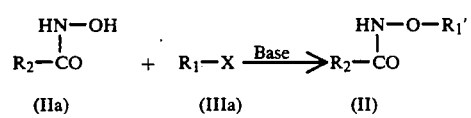

(IIa)   (IIIa)   (II)

where X, $R_1$, $R_1'$ and $R_2$ are as defined above.

The compounds of formula (II) are prepared by reacting a compound of formula (IIa) with a compound of formula (IIIa) in the presence of a base; and protecting any hydroxy groups present in $R_1$ with a hydroxy protecting group as described above. The base used can be an organic or inorganic base, such as those described above, in particular sodium or potassium hydroxide. It is preferred that the reaction be carried out in an inert solvent, for example, lower alkanols such as methanol or ethanol, ethers such as dioxane, or tetrahydrofuran. It is also preferred that the reaction be run at temperatures between about $20°$ C. to about $100°$ C., especially about $30°$ C. to about $70°$ C. The time of the reaction is not critical; but it is preferred that the reaction be run for about 5 to 48 hours, especially 12 to 30 hours. The compound of formula (II) is isolated by conventional techniques, for example, evaporation, chromatography, and recrystallization.

Many of the compounds of formula (III), (IIIa), (IV), (V), and (VI) are known and may be prepared by methods described in the literature. The starting materials not specifically disclosed in the art may be prepared by analogous methods or as described in the examples below using known starting materials.

As indicated above, the compounds of formula (I) exhibit pharmacological activity in animals. In particular, the compounds of formula (I) are anti-diabetic agents and are useful in the treatment of diabetes, as indicated by the chronic hypoglycemic screen test in male Sprague-Dawley rats, given 1 to 100 mg/kg/day of drug orally. The rats, 2 to 3 months of age, weighing 200 to 220 grams, are kept in a room at a controlled ambient temperature of 72° F. and a 12/12 hour light-/dark cycle for one week before and during testing. In the chronic screen test, the rats are fed a high fat diet ad libitum. At fed state, 40 mg of streptozotocin/kg body weight are injected via the tail vein. One week later, those rats are considered to be diabetic which have fed blood glucose of greater than 200 mg/dl and, following an overnight fast, when given an oral glucose tolerance test have blood glucose of 41 to 80 mg/dl 3 hours after the test. Blood glucose is determined with a YSI Glucose Analyzer. The chronic screen test is carried out as follows:

On Day 1, food is removed from rats at 9:00 A.M.; and after an initial blood glucose reading is taken via the tail vein, vehicle (control) or compound (9 rats/treatment) is administered orally. Six hours later blood glucose level is measured and immediately thereafter the rats are refed. The same rats are given either vehicle or drug once a day for 11 consecutive days. Blood glucose is then determined after a 6-hour fast post dosing on days 4, 8, and 11. The ED50 value is the amount of compound required to produce a 50% reduction on day 11 of the average increase in blood glucose level induced by streptozotocin.

The compounds of formula (I) are also hypolipidemic agents and are useful in lowering cholesterol and triglycerides as measured in the above Sprague-Dawley rats following the chronic hypoglycemia determination. After the glucose sample is removed on day 11, the rats are sacrificed; and blood serum is collected and adjusted to a density of 1.06 grams/ml. with sodium chloride. The density adjusted blood serum is centrifuged at 42,000 rpm in a Beckmann 42.2 Ti rotor at 20° C for 2.5 hours in a Beckmann L8-M ultracentrifuge. Ninety-five μL is fractionated from the top of the centrifuged mixture (LDL fraction) leaving 80 μL in the bottom (HDL fraction). Cholesterol is determined with the Sigma Diagnostic kit for the enzymatic determination of cholesterol, procedure No, 352, modified for use with 96 well microliter plates. Twenty microliters of calibrator, standard, or sample are mixed with 200 microliter aliquots of enzyme reagent in the 96 wells and incubated at ambient temperature for 15 minutes. Total cholesterol and HDL are determined by absorbance measurement at 500 nM with a colorimetric micrometer plate reader. LDL is determined by subtracting HDL from total cholesterol. Total triglycerides in the blood serum are determined using the Boehringer Mannheim Diagnostic Reagents set R Triglycerides-GB kit modified for microtiter plate assays as follows: the contents of bottle 2 (enzymes) and bottle 3 (lipase +4-aminoantipyrine) are each diluted to 8 ml. with buffer (bottle 1) and stored in 2 ml. aliquots in cryovials at −90° C. Ten ml. of buffer is added to a 2 ml. aliquot of diluted enzymes and to a 2 ml. aliquot of diluted lipase +4-aminoantipyrine to form working solutions 1 and 2, respectively. One hundred μl of working solution 1 and 20 μl of dilute blood serum (1:1 blood serum:saline) are added to each well of a ninety-six microtiter plate and mixed and incubated at 20°-25° C. for at least 5 minutes. One hundred μl of working solution 2 is added to each well, and the contents of each well are mixed, and again incubated at 20°-25° C. for at least 5 minutes. Absorbance is measured at 500 nM, and total triglyceride contents in mg/dl of blood serum is calculated by comparing the absorbance with the absorbance of known samples.

The antidiabetic and hypolipidemic effective dosage of the compounds of formula (I) employed for the alleviation of the above conditions will vary depending on the particular compound employed, the mode of administration and severity of the condition being treated. However, in general, satisfactory results are obtained when the compounds of formula (I) are administered at a daily dosage of from about 1 milligram to about 100 milligrams per kilogram of animal body weight, optionally given in divided doses two to four times a day, or in sustained release form. For the larger mammals, for example primates such as humans, the total daily dosage is from about 5 to about 500 milligrams per day. Unit dosage forms comprise from about 1 to about 500 milligrams of the active compound in intimate admixture with a solid or liquid pharmaceutically acceptable carrier or diluent. The compounds of the invention may be administered in a manner similar to known standards for the above uses. The suitable daily dosage for a particular compound will depend on a number of factors, such as its relative potency of activity. It has been determined that the preferred compound of the invention N-methoxy-4-pivaloylbenzimidic acid, 4-pivaloylbenzoic acid anhydride or alternatively 4-pivaloylbenzoyl-N-methoxy-4-pivaloylbenzimidate, has an ED50 of 28 mg/kg in the chronic hypoglycemia test. An indicated daily dose for the compound is from about 100 to about 500, preferably 150 to 250 mg p.o. for the larger primates, such as humans.

For the above use, the compounds of formula (I) may be administered orally or parenterally as such or admixed with conventional pharmaceutical carriers. They may be administered orally in such forms as tablets, dispersible powders, granules, capsules, syrups and elixirs, and parenterally as solutions or emulsions. These pharmaceutical preparations may contain up to about 90% of the active ingredient in combination with the carrier or adjuvant.

Capsules containing the ingredients indicated below may be prepared by conventional techniques and are useful in treating diabetes at a dose of one or two capsules two to four times a day.

| Ingredient | Weight (mg) |
|---|---|
| 4-pivaloyl-N-methoxy-4-pivaloylbenzimidate | 250 |
| Lactose | 445 |
| Colloidal silicon | 50 |
| Stearic acid | 5 |
| | 750 |

EXAMPLE 1

4-pivaloylbenzoyl-N-methoxy-4-pivaloylbenzimidate

Step A) 4-pivaloylbenzoyl chloride 84 grams of 4-pivaloyl-benzoic acid in 210 milliliters of thionyl chloride are refluxed under nitrogen for about 1½ hours. The excess thionyl chloride is then stripped off under reduced pressure to yield the crystalline acid chloride (m.p. 38°-39° C.).

Step B) N-methoxy-4-pivaloylbenzamide 48.9 grams of methoxyamine hydrochloride are added with stirring to a mixture of 660 milliliters of 1.5N sodium hydroxide and 600 milliliters of tetrahydrofuran (THF) at 5° C. After 30 minutes, 87.8 grams of 4-pivaloylbenzoyl chloride dissolved in 150 milliliters of THF is added at 5 to 10° C. The mixture is stirred at 5° C. for 30 minutes, following which the THF is evaporated off to yield a slurry. The slurry is extracted four times with 500 milliliters of methylene chloride, and then the combined organic layers are washed with 5% sodium bicarbonate and saturated sodium chloride. The organic layer is dried over magnesium sulfate and concentrated to about 300 milliliters. 600 milliliters of heptane is added to crystallize out N-methoxy-4-pivaloylbenzamide (m.p. 125°–126.5° C).

Following the above procedure of steps A and B and using in place of the 4-pivaloylbenzoic acid an equivalent amount of:
a) acetic acid;
b) pivalic acid;
c) benzoic acid;
d) *p*-hydroxybenzoic acid;
e) *p*-chlorobenzoic acid;
f) *p*-toluic acid; or
g) *p*-methoxybenzoic acid,
there is obtained
a) N-methoxy-acetamide;
b) N-methoxy-pivalamide;
c) N-methoxy-benzamide;
d) N-methoxy-*p*-hydroxybenzamide;
e) N-methoxy-*p*-chlorobenzamide;
f) N-methoxy-*p*-toluamide; or
g) N-methoxy-*p*-methoxybenzamide,
respectively.

When the above reaction is carried out using in place of the methoxyamine an equivalent amount of the following:
h) isopropoxyamine;
i) allyloxyamine;
j) phenoxyamine;
k) benzyloxyamine; or
l) t-butoxyamine,
there is obtained
h) N-isopropoxy-4-pivaloylbenzamide;
i) N-allyloxy-4-pivaloylbenzamide;
j) N-phenoxy-4-pivaloylbenzamide;
k) N-benzyloxy-4-pivaloylbenzamide; or
l) N-(t-butoxy)-4-pivaloybenzamide, respectively.

Step C)
4-pivaloylbenzoyl-N-methoxy-4-pivaloylbenzimidate 23.5 grams (100 mmol) of 4-pivaloyl-N-methoxybenzamide, 16.0 grams (158 mmol) of triethylamine and 300 milliliters of toluene are stirred together for 15 minutes at 20° C. The mixture is then cooled to −8° C., and 24.7 grams (110 mmol) of 4-pivaloylbenzoyl chloride in 200 milliliters of toluene are added at −8° C. to −5° C. over a period of 30 minutes. The mixture is allowed to warm slowly to 22° C. over 30 minutes and is stirred at that temperature for an additional 30 minutes. It is then heated to 55° C. over 15 minutes and maintained at 45° to 50° C. for 1 hour. The mixture is then cooled to 22° C., and 300 ml of water are added. After stirring for 10 minutes at 20° C., the water is discarded; and the organic phase is washed two more times with 250 milliliter portions of water. The toluene phase is then evaporated to a white solid; and the crude product obtained is recrystallized from 300 milliliters of 1:2 toluene/heptane to yeild 4-pivaloylbenzoyl-N-methoxy-4-pivaloylbenzimidate (m.p 104° C.–104.8° C.).

Following the above procedure and using in place of the 4-pivaloyl-N-methoxybenzamide, an equivalent amount of
a) N-methoxy-acetamide;
b) N-methoxy-pivalamide;
c) N-methoxy-benzamide;
d) N-methoxy-*p*-hydroxybenzamide;
e) N-methoxy-*p*-chlorobenzamide;
f) N-methoxy-*p*-toluamide;
g) N-methoxy-*p*-methoxybenzamide;
h) N-isopropoxy-4-pivaloylbenzamide;
i) N-allyloxy-4-pivaloylbenzamide;
j) N-phenoxy-4-pivaloylbenzamide;
k) N-benzyloxy-4-pivaloylbenzamide;
l) N-(t-butoxy)-4-pivaloylbenzamide;
m) N-(2-methoxyethoxy)-4-pivaloylbenzamide; or
n) N-(4-pivaloylbenzyloxy)-4-pivaloylbenzamide,
there is obtained
a) 4-pivaloylbenzoyl-N-methoxy-acetimidate, $^1$HNMR (CDCl): 1.35 (9H,s), 2.17 (3H,s), 3.84 (3H,s), 7.71 (2H,d), 8.16 (2H,d);
b) 4-pivaloylbenzoyl-N-methoxy-pivalimidate (m.p. 60°–62° C.);
c) 4-pivaloylbenzoyl-N-methoxy-benzimidate (m.p. 105°–107° C.);
d) 4-pivaloylbenzoyl-N-methoxy-*p*-hydroxybenzimidate;
e) 4-pivaloylbenzoyl-N-methoxy-*p*-chlorobenzimidate;
f) 4-pivaloylbenzoyl-N-methoxy-*p*-toluimidate;
g) 4-pivaloylbenzoyl-N-methoxy-*p*-methoxybenzimidate;
h) 4-pivaloylbenzoyl-N-isopropoxy-4-pivaloylbenzimidate (m.p. 76° C.);
i) 4-pivaloylbenzoyl-N-allyloxy-4-pivaloylbenzimidate (m.p. 76° C.);
j) 4-pivaloylbenzoyl-N-phenoxy-4-pivaloylbenzimidate (m.p. 143° C.);
k) 4-pivaloylbenzoyl-N-benzyloxy-4-pivaloylbenzimidate (m.p. 126° C.);
l) 4-pivaloylbenzoyl-N-(t-butoxy)-4-pivaloylbenzimidate;
m) 4-pivaloylbenzoyl-N-(2-methoxyethoxy)-4-pivaloylbenzimidate; $^1$H NMR(CDCl$_3$): 1.32 ppm (9H,s), 1.33 (9H,s), 3.32 (3H,s), 3.68 (2H, t, J =7 Hz), (4.32, t, J=7 Hz), 7.63–7.85 (6H, m), 8.21 (2H, m) or
n) 4-pivaloylbenzoyl-N-(4-pivaloylbenzyloxy)-4-pivaloylbenzimidate,
respectively.

Following the above procedure and using in place of the 4-pivaloylbenzoyl chloride an equivalent amount of
o) acetyl chloride;
p) pivaloyl chloride;
q) benzoyl chloride; or
r) benzyl chloride,
there is obtained
o) acetyl-N-methoxy-4-pivaloylbenzimidate (m.p. 32° C.-34° C.);
p) pivaloyl-N-methoxy-4-pivaloylbenzimidate (m.p. 48° C.-50° C.);
q) benzoyl-N-methoxy-4-pivaloylbenzimidate (m.p. 63° C.-65° C.); or
r) benzyl-N-methoxy-4-pivaloylbenzimidate,
respectively

EXAMPLE 2

4-pivaloylbenzoyl-N-(2-hydroxyethoxy)-4-pivaloylbenzimidate

Step A) N-(2-hydroxyethoxy)-4-pivaloylbenzamide

To a solution of 4.0 grams (18.1 mmol) of N-hydroxy-4-pivaloylbenzamide in 10 milliliters of ethanol is added an aqueous solution of 725 milligrams (18.1 mmol) of sodium hydroxide in 1 milliliter of water. To this is added 1.67 milliliters (23.6 mmol) of 2-bromoethanol; and the resulting mixture is heated at 55° C. for 24 hours. The mixture is cooled to 20° C., concentrated, and extracted 3 times with 10 milliliters of chloroform. The combined extracts are washed with 15 milliliters of water and then 15 milliliters of brine, dried over magnesium sulfate and concentrated. The residue is recrystallized from methylene chloride/hexane (1:4) to yield N-(2-hydroxyethoxy)-4-pivaloylbenzamide.

When an equivalent amount of methyl-2-bromoethyl ether, 3-bromo-1,2-propylene glycol, isopropyl bromide, allyl bromide, benzyl bromide, or 4-pivaloylbenzylbromide is used in place of the 2-bromoethanol in the above procedure, there is obtained N-(2-methoxyethoxy)-4-pivaloylbenzamide, N-(2,3-dihyroxypropoxy)-4-pivaloylbenzamide, N-isopropoxy-4-pivaloylbenzamide, N-allyloxy-4-pivaloylbenzamide, N-benzyloxy-4-pivaloylbenzamide, or N-(4-pivaloylbenzyloxy)-4-pivaloylbenzamide respectively.

Step B) 4-pivaloylbenzoyl-N-(2-hydroxyethoxy)-4-pivaloylbenzimidate

To a solution of 2.8 grams (10.6 mmol) of N-(2-hydroxy-ethoxy)-4-pivaloylbenzamide in 5 ml of methylene chloride and 3 ml of pyridine at 0° C. are added 3.92 grams (12.7 mmol) of p-anisylchlorodiphenylmethane. The mixture is warmed to room temperature over two hours and then diluted with 40 ml of methylene chloride. This solution is washed with 50 ml of 10% sodium bicarbonate and 30 ml of brine, dried over magnesium sulfate and concentrated by evaporation. The residue is purified by column chromatography using 5:1 hexane/ethyl acetate as the eluent to obtain the protected product, N-(2-[p-anisyldiphenylmethyloxy]ethoxy)-4-pivaloylbenzamide.

To a solution of 5.25 grams (9.7 mmol) of N-(2-[p-anisyldiphenylmethyloxy]ethoxy)-4-pivaloylbenzamide in 20 ml of THF at 0° C. is added 700 milligrams of hexane washed potassium hydride; and after 20 minutes, 2.3 grams (10.2 mmol) of 4-pivaloylbenzoyl chloride are added. This mixture is allowed to warm to room temperature and stirred for one hour following which it is poured into 50 ml of saturated ammonium chloride and extracted twice with 50 ml of t-butyl methyl ether. The combined organic layers are washed with 50 ml of water and 50 ml of brine, then dried over magnesium sulfate and evaporated to dryness. The crude product is dissolved in 30 ml of THF at 0° C., and 0.75 ml of 2 N hydrochloric acid is added. This mixture is stored at 0° C. for 60 hours. After deprotection is complete, the mixture is poured into 100 ml of 10% sodium bicarbonate and extracted twice with 100 ml of ethyl acetate. The combined organic layers are washed with 50 ml of water and 50 ml of brine, dried over magnesium sulfate and concentrated by evaporation. The product is purified by column chromatography using of 1:1 hexane/ethyl acetate as the eluant and recrystallized from 3:1 hexane/chloroform to yield 4-pivaloylbenzoyl-N-(2-hydroxyethoxy)-4-pivaloylbenzimidate (m.p. 106° C.).

EXAMPLE 3

4-pivaloylbenzoyl-N-(2,3-dihyroxypropoxy)-4-pivaloylbenzimidate

To a solution of 4.0 grams (13.6 mmol) of N-(2,3-dihydroxypropoxy-4-pivaloylbenzamide in 30 milliliters of acetone is added 10 mg of p-toluenesulfonic acid, following which 250 µl of 2,2-dimethoxypropane is added dropwise over 20 minutes. After an additional 40 minutes of stirring, the mixture is quenched with 50 mg of solid sodium bicarbonate and concentrated. The residue is extracted with methylene chloride; and the extract is evaporated to dryness to yield the acetonide,N-[(2,2-dimethyl-1,3-dioxolan-4-yl) methoxy]-4-pivaloylbenzamide.

Following the procedure of example 2 and using an equivalent amount of the above acetonide in place of the N-2-[p-anisyldiphenylmethyloxy]ethoxy)-4-pivaloylbenzamide, there is obtained 4-pivaloylbenzoyl-N-[(2,2-dimethyl-1,3-dioxolan-4-yl)-methoxy]-4-pivaloylbenzimidate. This compound is dissolved in 30 ml of THF and 3 ml of water, and 0.5 ml of 2N hydrochloric acid is added. The mixture is stirred for 2 hours at room temperature, after which 50 ml of saturated sodium bicarbonate is added. This aqueous mixture is extracted twice with 40 ml of ethyl acetate. The combined organic layers are washed with brine, dried over magnesium sulfate, and evaporated. The residue is recrystallized from methylene chloride/hexane (1:4) to yield 4-pivaloylbenzoyl-N-(2,3-dihyroxypropoxy)-4-pivaloylbenzimidate.

EXAMPLE 4

4-pivaloylbenzoyl-N-(2,3-dihyroxypropoxy)-4-pivaloylbenzimidate

The above 4-pivaloylbenzoyl-N-(2,3-dihyroxypropoxy)-4-pivaloylbenzimidate can also be prepared from 4-pivaloyl-benzoyl-N-allyloxy-4-pivaloylbenzimidate by hydroxylation in the following manner. To a solution of 4.0 grams (891 mmol) of 4-pivaloylbenzoyl-N-allyloxy-4-pivaloylbenzimidate and 2.1 grams (1.780 mmol) of N-methylmorpholine in 30 ml of 9:1 acetone:water is added 1 ml of a 1% solution of osmium tetroxide in butanol. This mixture is stirred for 24 hours at room temperature and then quenched with excess solid sodium meta bisulfite and concentrated by evaporation. The residue is extracted three times with 20 ml of ethyl acetate, and the combined extracts are filtered and again concentrated by evaporation. This residue is subjected to column chromatography using 1:1 hexane/ethyl acetate as the eluant and then recrystallized from 1:4 chloroform/hexane to yield 4-pivaloylbenzoyl-N-(2,3-dihyroxypropoxy)-4-pivaloylbenzimidate (m.p. 64°).

EXAMPLE 5

4-pivaloylbenzoyl-N-methoxy-4-pivaloylbenzimidate

A mixture of 30.94 grams (150 mmol) of 4-pivaloylbenzoic acid, 44.6 grams (375 mmol) of thionyl chloride and 1 drop of dimethylformamide (DMF) are heated slowly to 105° C. over a period of 1 hour and then refluxed at 105° to 107° C. for an additional 1 hour to obtain a yellow homogeneous mixture. Excess thionyl chloride is removed under vacuum at 50 to 70° C., and the residue is flashed twice under house vacuum with 50 ml of toluene. The mixture is cooled to −15° C. after adding 300 ml of toluene, and 29 grams (287 mmol) of triethylamine are added dropwise over 20 minutes while maintaining the temperature between −5° and −10° C. A solution of 6.27 grams (75 mmol) of methoxyamine hydrochloride in 150 ml of water is added over a period of 20 minutes, following which the mixture is allowed to warm to 22° C. over 30 minutes and then to 45° to 50° C., where it is maintained for 1 hour. The toluene layer is washed twice with 75 ml of water and filtered to remove trace amount of insolubles. The toluene is evaporated off at 50° to 60° C. under vaccum, and the crude product is dissolved in toluene at 65° to 70° C. After adding 160 ml of heptane, the solution is cooled to 17° C. over 15 minutes with stirring and maintained at 17° to 18° C. for 30 minutes. The slurry is fast filtered at 18° C., and the residue is washed with 35 ml of 1:4 toluene/heptane to yield, after drying overnight, 4-pivaloylbenzoyl-N-methoxy-4-pivaloylbenzimidate (m.p. 103°–104° C.).

EXAMPLE 6

4-pivaloylbenzoyl-N-methoxy-4-pivaloylbenzimidate

Step A. 4-(2,2-dimethyl-1-oxopropyl)-benzoyl chloride

A mixture of 150.0 g (0.725 mol) of 4-(2,2-dimethyl-1-oxopropyl)-benzoic acid and 0.3 ml of dimethylformamide are added with stirring at 22° C. to 30° C. to 180 ml (2.47 mol) of thionyl chloride over a period of 60 minutes. The resulting solution is heated to an internal temperature of 85° to 90° C., and maintained at this temperature for 15 minutes. The solution is allowed to cool to 50° C. to remove as much thionyl chloride as possible by vacuum distillation (20–30 torr) at an internal temperature of 45° to 55° C. Distillation is discontinued when the internal temperature reaches 55° C and 95 ml of dry toluene are added. The distillation is continued under vacuum at an internal temperature of 45° to 55° C. and again discontinued when the internal temperature reaches 55° C. at 20–30 torr. After allowing the residue to cool to 25° C. and diluting it with 950 ml of dry toluene, the solution is set aside for use below.

Step B.
4-pivaloylbenzoyl-N-methoxy-4-pivaloylbenzimidate

At room temperature, 101.3 g (0.373 mol) of 30.8% aqueous methoxyamine hydrochloride solution is diluted with 500 mL of deionized water. To this solution is added 165.3 g (1.636 mol) of triethylamine at a rate such that the internal temperature remains between 22° C. and 30° C. over a period of 5 to 10 minutes. This solution is cooled to an internal temperature of −7° to −10° C.; and then slowly with efficient stirring, the acid chloride solution of step A is added over a period of 45 to 60 minutes while maintaining the internal temperature between −5° and −7° C. The reaction mixture is allowed to warm to 22° C. over a period of 60 minutes and then warmed to 33° to 35° C. over a period of 15 minutes and maintained at this temperature for an additional 20 minutes. The layers are separated and 285 ml of saturated aqueous sodium carbonate solution is added to the organic layer. The mixture is stirred vigorously for about 15 to 20 minutes to insure good mixture of the two phases. After stirring, the layers are separated and the upper organic layer is washed with three 285-ml portions of deionized water. The toluene layer is then rapidly filtered through 50 g of Celite to remove any insolubles and the filter cake is rinsed with 50 ml of toluene. After filtering, the combined organic phases are stripped under vacuum (20–30 torr) at 55° to 60° C. to yield a yellow oil, which is dissolved at 50° to 55° C. in a mixture of 1100 ml of methyl alcohol and 57 ml of toluene. The solution is heated at reflux (ca. 65° C.) for 30 to 45 minutes and then cooled to 22° C. with stirring over a 1 hour period. Agitation is continued for an additional 30 to 45 minutes at a temperature of 22° to 25° C., and the solids formed are collected by filtration. The filter cake is washed with 60 ml of cold (0° to 5° C.) methyl alcohol; and the solids are dried in vacuo (25 to 30 torr) at 60° to 70° C for 16 to 24 hours to yield (4-pivaloylbenzoyl-N-methoxy-4-pivaloylbenzimidate); m.p. 104.5° C.

EXAMPLE 7

4-pivaloylbenzoyl-N-carboxymethoxy-4-pivaloylbenzimidate

Step A)
N-(t-butoxycarbonylmethoxy)-4-pivaloylbenzamide

To 0.8 gram (20 mmol) of sodium hydroxide in 75 ml of ethanol are added 4.42 grams (20 mmol) of N-hydroxy-4-pivaloylbenzamide prepared as in step B of example 1 using an equivalent amount of hydroxylamine in place of the methoxyamine, followed by 3.6 ml (22.3 mmol) of t-butyl-bromoacetate. The reaction mixture is allowed to reflux for 6 hours; and after cooling, the sodium bromide formed is filtered off; and 75 ml of diethyl ether are added. The filtrate is evaporated under reduced pressure, and the residue is purified on a 2 inch flash column using 1000 ml of 1.5% methanol/chloroform to elute the column. After evaporation, the product is crystallized from 1:4 ether/hexane to yield N-(t-butoxycarbonylmethoxy)-4-pivaloylbenzamide (m.p. 87°–88° C.).

Following the above procedure, and using in place of the t-butyl-bromoacetate an equivalent amount of
t-butoxy-4-bromo-n-butyrate or
t-butoxy-2-bromoisobutyrate,
there is obtained
N-(t-butoxycarbonylpropoxy)-4-pivaloylbenzamide or
N-[2-(t-butoxycarbonyl)-2-propoxy]-4-pivaloylbenzamide,
respectively.

Step B)
4-pivaloylbenzoyl-N-(t-butoxycarbonylmethoxy)-4-pivaloylbenzimidate

To a solution of 2.0 grams (6.0 mmol) of the N-(t-butoxycarbonylmethoxy)-4-pivaloylbenzamide of step A in 30 ml of THF are added 1.1 ml (7.9 mmol) of triethylamine followed dropwise by 1.6 gram (7.1 mmol) of 4-pivaloylbenzoyl chloride in 10 ml of THF. The reaction mixture is allowed to stir for 2 hours at room temperature; and after adding 50 ml of diethyl ether, the mixture is filtered to remove the triethylamine hydrochloride formed and then evaporated under reduced pressure. The residue is purified on a 2 inch flash column using 1500 ml of dichloromethane to elute the column. After evaporation, white crystalline 4-pivaloylbenzoyl-N-(t-butoxy-carbonylmethoxy)-4-pivaloylbenzimidate (m.p. 112°–115° C.) is obtained.

When the above reaction is carried out using in place of the N-(t-butoxycarbonylmethoxy)-4-pivaloylbenzamide, an equivalent amount of N-(t-butoxycarbonylpropoxy)-4-pivaloylbenzamide or N-[2-(t-butoxycarbonyl)-2-propoxy]-4-pivaloylbenzamide, there is obtained 4-pivaloylbenzoyl-N-(t-butoxycarbonylpropoxy)-4-pivaloyl-benzimidate (m.p. 65°-67° C.) or 4-pivaloylbenzoyl-N-[2-(t-butoxycarbonyl)-2-propoxy]-4pivaloylbenzimidate (oil), respectively.

Step C)
4-pivaloylbenzoyl-N-carboxymethoxy-4-pivaloylbenzimidate

A solution of 2.3 grams (4.4 mm) of 4-pivaloyl-benzoyl-N-(t-butoxycarbonylmethyl)-4-pivaloylbenzimidate in 50 ml of 5% triflouroacetic acid in chloroform is allowed to stand at room temperature for 3½ hours. The reaction mixture is evaporated under reduced pressure, and the residue is crystallized from 1:4 ether/hexane to yield 4-pivaloyl-benzoyl-N-carboxymethoxy-4-pivaloylbenzimidate (m.p. 72°-74° C.)

Following the above procedure, and using in place of the 4-pivaloylbenzoyl-N-(t-butoxycarbonylmethoxy)-4-pivaloylbenzimidate, an equivalent amount of 4-pivaloylbenzoyl-N-(t-butoxycarbonylpropoxy)-4-pivaloylbenzimidate or 4-pivaloylbenzoyl-N-[2-(t-butoxycarbonyl)-2-propoxy]-4-pivaloylbenzimidate there is obtained 4-pivaloylbenzoyl-N-carboxypropoxy-4-pivaloylbenzimidate (m.p. 125°-126° C.) or 4-pivaloylbenzoyl-N-(2-carboxy-2-propoxy)-4-pivaloylbenzimidate (m.p. 95°-97° C.), respectively.

What is claimed is:

1. A process for the preparation of a compound of the formula:

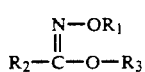 (I)

where
$R_1$ is alkyl of 1 to 6 carbon atoms; alkenyl of 3 to 5 carbon atoms, wherein the double bond is separated from the oxygen atom by at least 2 carbon atoms; alkyl or 2 to 8 carbon atoms mono- or poly substituted on other than the α-carbon by 1 to 7 hydroxy groups; or alkyl of 2 to 8 carbon atoms mono- or poly-substituted by 1 to 7 lower alkoxy groups, or carboxyalkyl of 2 to 6 carbon atoms, or

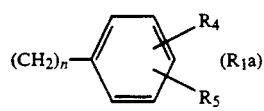

where
$R_4$ and $R_5$ are each independently hydrogen, halogen, hydroxy, lower alkyl, or lower alkoxy and
n is 0 or an integer of 1 to 5,
$R_2$ is lower alkyl,

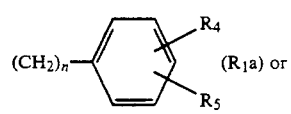 or

-continued

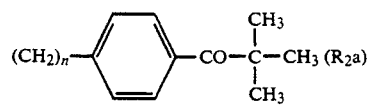 ($R_{2a}$)

where
n, $R_4$, and $R_5$ are as defined above, and $R_3$ is CO—$R_2$, where
$R_2$ is as defined above,
with the provisos:
a) when $R_3$ is CO—$R_{1a}$ or CO—$R_{2a}$, n is O; and
b) when $R_3$ is other than CO—$R_{2a}$, $R_2$ is $R_{2a}$ in which n is O, which comprises reacting a compound of the formula

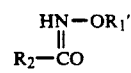

where $R_1'$ is the same as $R_1$ but with any hydroxy or carboxy group present protected by a hydroxy or carboxy protecting group, with a compound of the formula

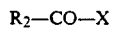

where X is a leaving group, in the presence of hindered organic base; and when a protected hydroxy or carboxy group is present in substituent $R_1'$, deprotecting the substituent.

2. A process according to claim 1 in which the hindered organic base is a tertiary amine.

3. A process according to claim 1 in which the reaction is carried out in a non-polar solvent.

4. The process according to claim 1, in which the compound of formula (I) is 4-pivaloylbenzoyl-N-methoxy-4-pivaloyl-benzimidate.

5. A process for the preparation of a compound of the formula

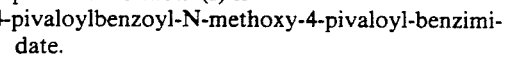 (Ia)

wherein
$R_1$ is as defined in claim 1 and
$R_2'$ is 4-pivaloylphenyl,
which comprises reacting a compound of the formula

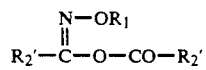 (IV)

where
X is a leaving group, with a hindered organic base of the formula

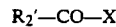 (V)

where
$R_6$, $R_7$, and $R_8$ are each lower alkyl or aryl, and with ½ mole of a compound of the formula

 (VI)

per mole of compound (IV), where $R_1'$ is as defined in claim 1, and deprotecting the product obtained when a protected hydroxy or carboxy group is present in the substituent R₁'.

6. A process according to claim 5, in which the hindered organic base is triethylamine.

7. The process according to claim 5, in which the compound of formula (Ia) is
4-pivaloylbenzoyl-N-methoxy-4-pivaloylbenzimidate.

8. A process according to claim 5 in which a compound of formula (IV) in a non polar solvent is reacted with an aqueous solution of a compound of formula (V) and a compound of formula (VI), in a mole ratio of the compound of formula (IV) to the compound of formula (VI) of 2:1.

9. A process according to claim 5 in which the reaction is carried out in a 2 to 3 moles of the compound of formula (V) per mole of compound of formula (IV).

10. A process according to claim 5 in which the reaction is carried out at −10° to 40° C.

11. A process according to claim 8 in which the nonpolar solvent is toluene.

12. A process according to claim 8 in which the final product is recrystallized from 5% toluene in methanol.

13. The process according to claim 8 in which the product is 4-pivaloylbenzoyl-N-methoxy-4-pivaloylbenzimidate.

* * * * *